United States Patent [19]

Schulze

[11] 4,115,446

[45] Sep. 19, 1978

[54] POLYETHER POLYUREIDES

[75] Inventor: Heinz Schulze, Austin, Tex.

[73] Assignee: Texaco Development Corp., New York, N.Y.

[21] Appl. No.: 743,879

[22] Filed: Nov. 22, 1976

[51] Int. Cl.$^2$ .............. C07C 127/15; C08G 65/32
[52] U.S. Cl. .............. 260/553 R; 260/45.9 NC; 528/111
[58] Field of Search .......... 260/553 R, 47 EN, 2 A

[56] References Cited

U.S. PATENT DOCUMENTS

| | | | |
|---|---|---|---|
| 3,324,176 | 6/1967 | Kirschnek et al. | 260/553 |
| 3,386,955 | 6/1968 | Nawakowski et al. | 260/47 |
| 3,386,956 | 6/1968 | Nawakowski et al. | 260/47 |
| 3,717,612 | 2/1973 | Babayan | 260/47 EN |
| 4,002,598 | 1/1977 | Waddill et al. | 260/47 EN |

Primary Examiner—Harold D. Anderson
Assistant Examiner—Earl A. Nielsen
Attorney, Agent, or Firm—Carl G. Ries; Thomas H. Whaley; Kenneth R. Priem

[57] ABSTRACT

Novel polyether polyureides useful in the manufacture of plastics, sealants, molds, foams and coatings. The novel composition comprises a mono- or di-substituted ureido-terminated polyoxyalkylene prepared by reacting a primary amine-terminated polyoxyalkylene containing material with suitable substituted ureido forming compounds at temperatures in the range from about 20° C to about 150° C in a molar ratio of about one molecule of ureido forming material for each terminal primary amino group.

15 Claims, No Drawings

POLYETHER POLYUREIDES

BACKGROUND OF THE INVENTION

1. Field of the Invention

This invention generally pertains to ureido-terminated compounds; and, more particularly to substituted ureido-terminated polyoxyalkylene containing compounds.

Prior Art

Polyureides are generally well-known. These compounds have many well-known uses as polymeric thermoplastic resins.

Aliphatic or aromatic compounds having one or more ureylene groups are well known. Various ureas and substituted ureas, such as those disclosed in U.S. Pat. Nos. 3,294,749; 2,713,569, 3,386,956; 3,386,955; 2,855,372; and 3,639,338 are known.

Additionally, polyalkylenepolyamine-containing compounds having primary or secondary amine termination are shown to form ureylene containing compounds. For example, triethylenetetramine can be reacted with urea at temperatures of 120°C to 160°C to form thermoplastic resinous polymers soluble in alcohols, ketones, and esters but insoluble in hydrocarbons and only limitedly soluble in water.

It has now been discovered that a certain class of polyether primary amine terminated compounds form polyether containing substituted polyureides. These compounds are useful as epoxy resin additives. The higher aliphatic substituted compounds are useful as waxes and thermoplastic materials. Additionally, the compounds of the instant invention show utility in reducing punking of phenolic foams.

SUMMARY OF THE INVENTION

According to the broad aspect of the instant invention, a polyether polyureide comprises a mono- or di-substituted, ureido terminated polyoxyalkylene material.

According to one aspect the novel polyether mono- and di- substituted ureido compounds are formed by the reaction of a ureido forming compound with a polyoxyalkylenepolyamine of the formula

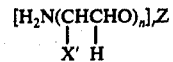

wherein X' is a hydrogen, a methyl radical or an ethyl radical; Z is a hydrocarbon radical having from 2 to 5 carbon atoms forming from 2 to 4 external ether linkages; n is a number from 1 to about 20 and r is a number from 2 to 4 in a molar ratio of one molecule of ureido group forming compound for each terminal primary amino group.

According to another aspect, the polyoxyalkylene polyamine material is first reacted with ureylene forming or thioureylene forming compounds to form a polyether urea or thiourea condensate having terminal primary amino groups. The condensate is then further reacted with a ureido forming compound in the above ratio to form a polyether urea or thiourea polyureido terminated material.

DESCRIPTION OF THE PREFERRED EMBODIMENT

According to a preferred embodiment, a mono-substituted polyureido terminated polyether is prepared by admixing and reacting a polyoxyalkylenediamine or triamine having a molecular weight from about 400 to 2,000 with a phenyl or lower alkyl isocyanate at temperatures of from about 50°C to about 200°C. The crude reaction product is then stripped at about 100°C to 110°C in vacuum to recover the product.

The novel substituted polyureido terminated polyethers in accordance with the instant invention are those compounds containing one or more polyoxyalkylene radicals and two or more ureides terminating the polyoxyalkylene chain. The ureides are monovalent substituted ureido groups of the formula

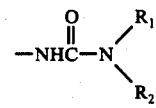

wherein $R_1$ and $R_2$ are, independently, hydrogen or a radical having the character of either an aliphatic or aromatic monovalent hydrocarbon moiety, provided at least one $R_1$ or $R_2$ is not hydrogen.

Suitable monovalent aliphatic radicals are saturated and unsaturated, acyclic and alicyclic radicals including the monocyclic and bridged alicyclic moieties.

In accordance with those suitable substituted ureido groups included herein, the moiety to which the

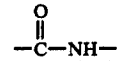

is attached, can consist of one or two hydrocarbon radicals joined to the included nitrogen through saturated carbon atoms and includes such radicals wherein the two carbons attached to the nitrogen are part of the same divalent hydrocarbon radical, which, together with the nitrogen, constitutes a cyclic secondary amino radical. It should further be realized that it is not critical that the radical(s) appended to the nitrogen be completely hydrocarbon. They may be substituted radicals such as oxa-, thia-, and aza- analogs of the corresponding hydrocarbons provided that the nitrogen with such attended radicals has the character of an aliphatic or cycloaliphatic nitrogen moiety.

Suitable monovalent aromatic radicals are mono- and poly-cyclic aromatics including the complex mono- and poly-cyclic arenes as well as the polycyclic aromatic compounds. It should be realized that it is not critical that the aromatic radical appended to the nitrogen be completely hydrocarbon so long as the moiety has the character of an monocyclic or polycyclic aromatic hydrocarbon radical. The aromatic radical can be substituted with saturated or unsaturated aliphatic moieties as described above, provided that the nitrogen with such appended radicals maintains the character of ureylene.

Preferably, $R_1$ and $R_2$ are independently hydrogen, provided only one is hydrogen; or alkyl, alkenyl, alkadienyl, alkatrienyl radicals of from 1 to 20 carbon atoms; or aryl, alkaryl or aralkyl monocyclic, polycyclic, or fused ring aromatic radicals of from 6 to 30 carbon atoms; or $R_1$ and $R_2$, taken together with the nitrogen atom to which each is attached, form a 5 or 6 membered heterocyclic ring such as morpholino, C-(alkyl substituted)morpholino, piperazino, C-(alkyl substituted)piperazino, pyrrolidino, and the like.

More preferably, $R_1$ and $R_2$, independently, are hydrogen, provided only one is hydrogen; or, are a branched or straight chain alkyl radical of from 1 to about 10 carbon atoms, and most preferably from 1 to about 4; or, are monocyclic aryl, alkaryl or aralkyl having from 6 to about 12 carbon atoms; or are branced or straight chain alkenyl or alkadienyl radical of from 2 to about 10 carbon atoms and most preferably 3 to about 8 carbon atoms.

In accordance with one preferred embodiment, $R_1$ and $R_2$, in the above formula, taken together with the nitrogen atom to which each is attached, form a heterocyclic ring. Preferably, such compounds are morpholines depicted by the formula

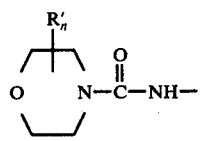

$R'$ is a lower alkyl radical such as methyl, ethyl and the like and $n$ is an integer from 0 to 4.

The polyether polyureides of the instant invention can be simply described as polyoxyalkylene containing compounds having terminal substituted ureido groups. In accordance with the greatly preferred embodiment, the substituted ureido terminated compounds are of the formula:

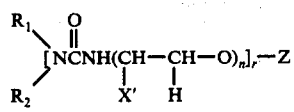

wherein $R_1$, $R_2$, $X'$, $Z$, $n$ and $r$ are as defined above. The most preferred polyoxyalkylenepolyureylenes are the polyoxypropylenediureylenes where $X'$ is a methyl radical; $n$ is a number from 2 to 17, $Z$ is a 1,2-propylene radical, $r$, is about 2 or 3 and $R_1$ and $R_2$ are independently hydrogen, provided only one is hydrogen; or a lower alkyl radical; a phenyl radical; or $R_1$ and $R_2$, taken together with the nitrogen to which they are attached, form a morpholino group.

According to another aspect, the polyureide compounds contain ureylene or thioureylene groups within the polyether chain. In accordance with this embodiment, a polyoxyalkylene ureylene or thioureylene having terminal primary amino groups is the oligomeric condensation product of a polyoxyalkylenepolyamine with a urea or thiourea forming compound. Compounds in accordance with this aspect of the invention can be depicted by the following formula

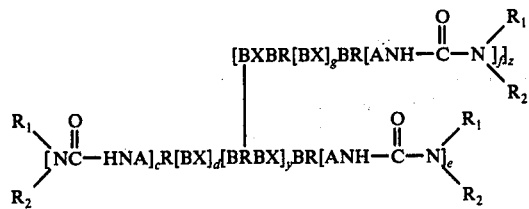

wherein A is a polyoxyalkylene radical containing from about 1 to 17 oxyalkylene groups, B is a polyoxyalkylene amino radical containing from about 1 to 17 oxalkylene groups, R is a hydrocarbon radical having from 2 to 5 carbon atoms and forming from 2 to 4 oxycarbon linkages with A and B, X is a C═O radical, a C═S radical or a radical derived from a difunctional isocyanate having two

groups, $c$ and $d$ are from 1 to 3 chosen such that their sum is from 1 to 4, $e$ is a number from 1 to 3, $f$ is a number from 1 to 3, $g$ is a number from 1 to 3, $y$ is a number from 0 to about 5, and $z$ is a number from 0 to 2; $R_1$ and $R_2$ are as defined herein above.

A preferred group of these compounds are depicted by the above formula wherein A corresponds to the formula:

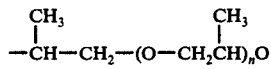

wherein $n$ is a number from 0 to 16 and preferably a number from 1 to 10, B corresponds to the formula:

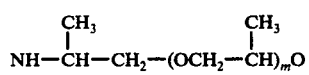

wherein $m$ is a number from 0 to 16 and preferably a number from 1 to 10, $c$ and $d$ are from 1 to 2 chosen such that their sum is from 2 to 3, $e$ is a number from 1 to 2, $g$ is a number from 1 to 2, $f$ is a number from 1 to 2, $z$ is a number from 0 to 1, $y$ is a number from 1 to 4, and X is a C═O radical and $R_1$ and $R_2$ are, independently, hydrogen; a lower alkyl radical; a phenyl radical; or $R_1$ and $R_2$, taken together with the nigrogens to which they are attached, form a morpholino group.

Generally, the substituted ureido terminated polyethers of the instant invention are formed by the reaction of the polyoxyalkylenepolyamines with a substituted ureido forming compound. The most preferred such compound is an isocyanate.

Generally, since the polyoxyalkylenepolyamine reactant already contains terminal primary amino groups, the compounds which supply the

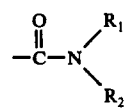

radical wherein $R_1$ and $R_2$ are as hereinbefore defined can be utilized.

When the mono-substituted product is desired, i.e., wherein $R_1$ is hydrogen, the amine terminated polyether is reacted with an isocyanate of the formula

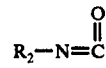

wherein $R_2$ is defined as above.

In accordance with this method, the reactants are simply admixed in correct molar ratios in a suitable reaction vessel and heated until the reaction occurs.

When di-substituted products are desired, other methods can be used to form the desired products. For example, substituted ureas of the formula:

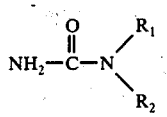

wherein $R_1$ and $R_2$ are defined as above can be utilized. However, this method is not preferred due to the tendency of the formed compounds to undergo rearrangement.

According to another method, a polyoxyalkylene containing polyisocyanate is reacted with a primary or secondary amine of the formula

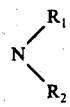

wherein $R_1$ and $R_2$ are defined as above.

The reaction between the polyoxyalkylene polyisocyanate and the primary or secondary is generally conducted at room or elevated temperatures, and in liquid phase.

The reactants as described hereinabove, are admixed in any desired manner so as to provide intimate admixture of reactants. A convenient way of carrying out the process is to introduce the reactants into a suitable reaction vessel equipped with heat transfer means and stirring means. The reactants may be added to the system in any order, either separately or first admixed with one another. Conveniently, the reaction is accomplished at temperatures which are sufficient to effect formation of the desired product.

The polyoxyalkylenepolyisocyanate material can be prepared by conventional phosgenation procedures well known in the art. The functionality of the polyoxyalkylene-polyisocyanate is dependent upon the number of terminal isocyanate groups.

It will be realized that each mole of amine reacts with a single isocyanate group of the polyoxyalkylenepolyisocyanate. It is particularly important that in forming the compounds of the instant invention a specific molar ratio of reactants be maintained. Specifically, about 1 molecule amine (ureido forming compound) for each isocyanate (amino) group of the polyoxyalkylenepolyisocyanate (amine) is required. Thus, for example, with a diisocyanate about 2 moles of amine compound is utilized. Preferably the instant reaction is carried out in the presence of a slight excess of amine compound to assure complete conversion of the isocyanate groups. The process is conveniently carried out at temperatures of from above about ambient ° C to about 200° C, and preferably from about 50° C to about 150° C, under pressure sufficient to maintain the reaction mass in liquid phase. Suitable such pressures include subatmospheric and superatmospheric pressures, however, the reaction is usally conducted at atmospheric pressure.

In accordance with another method, a secondary amine is phosgenated to produce the corresponding carbonyl chloride. The carbonyl chloride is then reacted with the diamine to produce the disubstituted ureido terminated products useful as additives in the instant invention.

Further methods of preparation include synthesis of the corresponding alkylene carbamate by use of an alkyl carbonate, i.e., phenyl carbamate in accordance with *Methoden Der Organischen Chemie*, Vol. VIII, , p. 161.

The polyoxyalkylene polyamines useful in forming the polyether poly substituted ureides of the instant invention may be depicted by the formula:

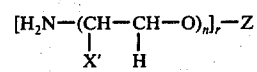

wherein X is hydrogen, a methyl radical or an ethyl radical; Z is a hydrocarbon radical having from 2 to 5 carbon atoms forming from 2 to 4 external ether linkages; n is a number from 1 to about 20 and r is a number from 2 to 4. The most preferred polyoxyalkylenepolyamines are the polyoxypropylenediamines wherein X' is a methyl radical, n is a number from 2 to 17, Z is a 1,2-propylene radical and r is about 2 or 3. These polyoxyalkylene polyamines can be prepared by known methods as disclosed in U.S. Pat. Nos. 3,236,895 and 3,654,370. Likewise, it is the above polyamines that are phosgenated to produce the corresponding isocyanates.

The polyether ureylene or thioureylene procursors that may be reacted with the substituted ureido forming compounds in accordance with this aspect of the instant invention can be depicted by the following formula:

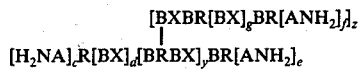

wherein A is a polyoxyalkylene radical containing from about 1 to about 17 oxyalkylene groups wherein each oxyalkylene group contains from 2 to about 4 carbon atoms; B is a polyoxyalkylene amino radical containing from about 1 to 17 oxyalkylene groups wherein each oxyalkylene group contains from 2 to about 4 carbon atoms; R is a hydrocarbon radical having from 2 to 5 carbon atoms forming from 2 to 4 oxycarbon linkages with A and B; X is a C=O radical, a C=S radical or a radical derived from a difunctional isocyanate having two

groups; c and d are from 1 to 3 chosen such that their sum is 2 to 4; e is a number from 1 to 3; f is a number from 1 to 3; g is a number from 1 to 3; y is a number from 0 to about 5; z is a number from 0 to 2.

Preferably these precursors are depicted by the above formula wherein A corresponds to the formula:

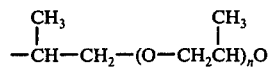

wherein n is a number from 0 to 16 and preferably a number from 1 to 10, B corresponds to the formula:

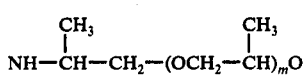

wherein $m$ is a number from 0 to 16 and preferably a number from 1 to 10, $c$ and $d$ are from 1 to 2 chosen such that their sum is from 2 to 3, $e$ is a number from 1 to 2, $g$ is a number from 1 to 2, $f$ is a number from 1 to 2, $z$ is a number from 0 to 1, $y$ is a number from 1 to 4, and X is a C=O radical.

These compounds are prepared by the well-known phosgenation of an amine which is reacted with the ureylene or thioureylene amine precursor above.

These polyether ureylenes can be formed by reaction of a polyoxyalkylenepolyamine wherein the alkylene contains from 2 to about 4 carbon atoms with urea, a ureylene forming compound, or an organic bifunctional isocyanate.

The primary amino terminated polyether thioureylene can be formed by reaction of a polyoxyalkylenepolyamine wherein the alkylene contains from 2 to about 4 carbon atoms with thiourea, a thioureylene forming compound or carbon disulfide.

The most preferred polyether thioureylene compound is that formed by reacting from about 5.0 mols to about 1.2 mols of polyoxypropylenepolyamine having a molecular weight of about 200 to about 2000 with 1 mol of carbon disulfide at temperatures from about 10° C to about 150° C. It has been found that addition of greater than about 0.5 moles of carbon disulfide per mole of polyoxyalkylenepolyamine produces highly viscous reaction mixtures. Therefore, suitable nondeleterious diluents well known in the art may be utilized to facilitate the reaction when greater than 0.5 moles of carbon disulfide is used per mole of polyoxyalkylenepolyamine.

A preferred class of polyoxyalkylenepolyamines useful in forming the polyether compounds may be depicted by the formula:

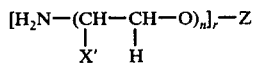

wherein X is hydrogen, a methyl radical or an ethyl radical; Z is a hydrocarbon radical having 2 to 5 carbon atoms forming from 2 to 4 external ether linkages; $n$ is a number from 1 to about 17 and $r$ is a number from 2 to 4. The most preferred polyoxyalkylenepolyamines are the polyoxypropylenediamines wherein X' is a methyl radical, $n$ is a number from 1 to 10, Z is a 1,2propylene radical and $r$ is about 2.

Whenever urea is employed as the reactant, the reaction proceeds with the evolution of ammonia. Since urea is bifunctional, each molecule of urea can react with two terminal amino groups of the polyoxyalkylenepolyamine. Consequently, it is possible to form polyureylenes in which the polyether ureylene unit repeats in the molecular structure.

While urea is the preferred reactant, other urea forming compounds may be utilized with the scope of the invention to supply the linking

radical. Since the polyoxyalkylenepolyamine reactant already contains terminal primary amino groups, compounds such as carbonyl diimidazole, phosgene, and diphenyl carbonate may be used to supply the

radical to form ureylene linkages without the liberation of ammonia.

Another class of polyether ureylenes which are useful are formed by reaction of polyoxyalkylenepolyamines with a bifunctional organic isocyanate obtained for instance from the phosgenated condensation product of aniline and formaldehyde. One suitable compound can be represented by the formula:

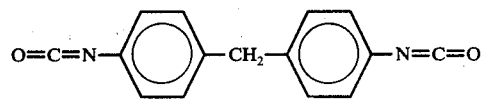

4,4'diphenylmethanediisocyanate or the isomers thereof such as 2,4'diphenylmethanediisocyanate. Mixtures of the isomers can also be used.

Whenever thiourea is employed as the reactant, the reaction proceeds with the evolution of ammonia. The functionality of the polyoxyalkylenepolyamine is dependent upon the number of terminal primary amino groups. Since thiourea, like urea, is bifunctional, each molecule of thiourea can react with two terminal amino groups of the polyoxyalkylenepolyamine. Consequently, it is possible to form polythioureylenes in which the thioureylene unit repeats in the molecular structure.

Whenever carbon disulfide is employed as the reactant in preparing the theourea precursor compounds, the reaction proceeds in two steps. The carbon disulfide is initially added to the reaction mixture at temperatures below the boiling point of carbon disulfide, e.g., less than 40° C. The reaction mixture is then heated to a temperature of from about 50° C to about 150° C until the evolution of hydrogen sulfide ceases. In this reaction, one mole of carbon disulfide will react with two moles of the polyoxyalkylenediamine to form the polyether thioureylene product.

While carbon disulfide is the preferred reactant, other thioureylene forming compounds may be utilized within the scope of the invention to supply the linking

radical. Since the polyoxyalkylenepolyamine reactant already contains terminal primary amino groups, compounds such as a dithioisocyanate, and thiophosgene can be used to supply the

radical to form thioureylene linkages.

Another class of polyether containing compounds which are useful in the practice of this invention, are mixed polyether ureylene-thioureylene compounds. Thus in accordance with this aspect of the invention radicals and

radicals are interspersed throughout the polyether chain to yield a mixed polyether ureylene-thioureylene.

The invention will be further illustrated by the following specific examples, which are given by way of illustration and not as limitations on the scope of this invention.

EXAMPLE I

In this example, a bis(N-substituted ureido) terminated material was prepared in accordance with the instant invention. Into a suitable reaction vessel, equipped with stirring apparatus, were charged 891 grams of a polyoxypropylenepolyamine having a molecular weight of approximately 2000, and an analysis of 1.01 milliequivalents (meq.) primary amine/g sold under the tradename "JEFFAMINE® D-2000" by Jefferson Chemical Company, Austin, Texas 78751. In a nitrogen atmosphere over a period of 45 minutes, 109 g of phenylisocyanate were added to the stirred polyoxypropylenediamine at a temperature of about 55°C. The temperature was raised to 60°C and the admixture was stirred an additional two hours. The corresponding bis(N-phenyl ureido) terminated compound was recovered and, upon analysis, showed 2.2% N; 0.009 meq total amine/g.

EXAMPLES II-VII

To illustrate the polyether ureide compounds of this invention, various epoxy formulations employing diglycidyl ether of 4,4'-isopropylidene bisphenol were cured with a polyoxypropylenediamine curing agent of m.w. 230 having an equivalent weight of 58 to which were added the indicated amounts of the diureide prepared in Example I. As indicated, a commercial accelerator was utilized. Three drops of silicone fluid were added to each formulation to prevent formation of voids and bubbles. After degassing under vacuum, the formulations were cured under the conditions indicated.

The resulting resins were used to bond aluminum to aluminum[1] and the resultant subjected to the American Society for Testing Materials (ASTM) test for tensile shear strength (ASTM D-1002-64). The data, which is for comparative purposes only, is presented in the following Table I.

(1) All substrates were aluminum panels (No. 2024-T-3 alloy, 16 gauge), degreased, then chromic acid etched prior to bonding.

TABLE I

| Formulation | \multicolumn{6}{c}{EXAMPLES} |
|---|---|---|---|---|---|---|
| | 2 | 3 | 4 | 5 | 6 | 7 |
| Epoxide, pbw (Eq. 190) | 100 | 100 | 100 | 100 | 100 | 100 |
| Curing agent, pbw[2] | 30 | 30 | 30 | 30 | 30 | 30 |
| Accelerator, pbw[3] | 10 | 10 | 10 | 10 | 10 | 10 |
| Diureide, pbw[4] | 0 | 5 | 10 | 20 | 30 | 40 |
| Tensile shear, psi[5] | 1500 | 1700 | 3400 | 3300 | 2800 | 2900 |

[2]Sold by Jefferson Chemical Company, Austin, Texas 78751 under the name "JEFFAMINE® D-230"
[3]A piperazine-alkanolamine admixture (30:70) sold by Jefferson Chemical Company, Austin, Texas 78751 under the name "Accelerator 398"
[4]The product of Example I
[5]Cure: 7 days, room temperature While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A polyether polyureide comprising a substituted ureido-terminated polyoxyalkylene selected from the group consisting of a compound of the formula:

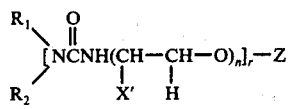

wherein $R_1$ and $R_2$ are, independently, hydrogen or an aliphatic or aromatic monovalent hydrocarbon radical, provided at least one $R_1$ or $R_2$ is not hydrogen; X' is hydrogen, a methyl radical or an ethyl radical; Z is a hydrocarbon radical having 2 to 5 carbon atoms forming from 2 to 4 external ether linkages; n is a number from 1 to about 20; and, r is a number from 2 to 4; and a compound of the formula:

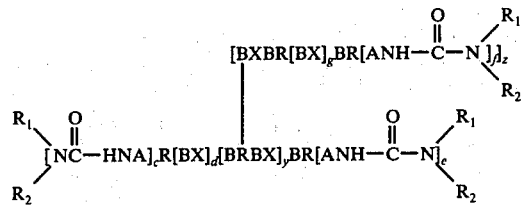

wherein $R_1$ and $R_2$ are as defined above; A is a polyoxyalkylene radical containing from about 1 to 17 oxyalkylene groups; B is a polyoxyalkylene amino radical containing from about 1 to 17 oxyalkylene groups; R is a hydrocarbon radical having from 2 to 5 carbon atoms and forming from 2 to 4 oxycarbon linkages with A and B; X is a C=O radical, a C=S radical or a radical derived from a difunctional isocyanate having two

groups; c and d are from 1 to 3 chosen such that their sum is from 1 to 4; e is a number from 1 to 3, f is a number from 1 to 3, g is a number from 1 to 3, y is a number from 0 to about 5, and z is a number from 0 to 2.

2. The polyether polyureide of claim 1 wherein X' is a methyl radical; n is a number from 2 to 17, Z is a 1,2-propylene radical and r is about 2 or 3.

3. The polyether polyureide of claim 1 wherein A corresponds to the formula:

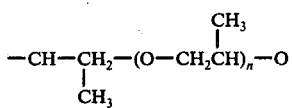

wherein n is a number from 0 to 15; B corresponds to the formula:

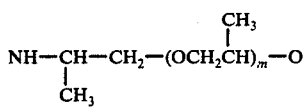

wherein m is a number from 0 to 15; c and d are from 1 to 2 and chosen so that their sum is from 2 to 3; e is a number from 1 to 2; g is a number from 1 to 2; f is a number from 1 to 2; z is a number from 0 to 1; y is a number from 1 to 4; and X is a C═O radical.

4. The polyether polyureide of claim 3 wherein n and m are, independently, numbers from about 1 to 10.

5. The polyether polyureide of claim 1 wherein X is the radical selected from a group consisting of

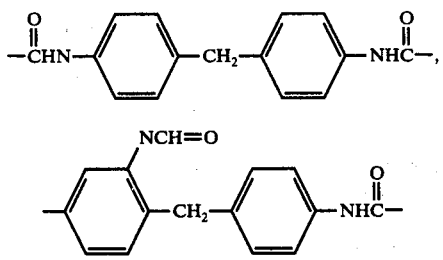

and mixtures thereof.

6. A polyether polyureide comprises a substituted ureido-terminated polyoxyalkylene material, formed by the reaction of a substituted ureido group forming compound with a compound selected from a polyoxyalkylenepolyamine of the formula

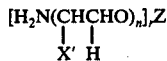

wherein X' is a hydrogen, a methyl radical or an ethyl radical; Z is a hydrocarbon radical having from 2 to 5 carbon atoms forming from 2 to 4 external either linkages; n is a number from 1 to about 20 and r is a number from 2 to 4 and a polyoxyalkylene ureylene or thioureylene having terminal primary amino groups of the formula

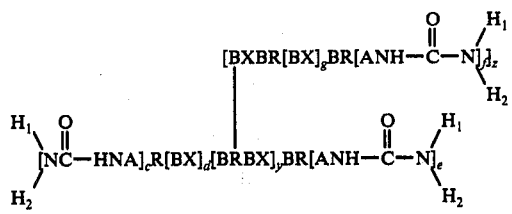

wherein A is a poloyxyalkylene radical containing from about 1 to about 17 oxyalkylene groups wherein each oxyalkylene group contains from 2 to about 4 carbon atoms; B is a polyoxyalkylene amino radical containing from about 1 to 17 oxyalkylene groups where each oxyalkylene group contains from 2 to about 4 carbon atoms; R is a hydrocarbon radical having from 2 to 5 carbon atoms forming from 2 to 4 oxycarbon linkages with A and B; X is a C═O radical, a C═S radical or a radical derived from a difunctional isocyanate having two

groups; c and d are from 1 to 3 chosen such that their sum is 2 to 4; e is a number from 1 to 3; f is a number from 1 to 3; g is a number from 1 to 3; y is a number from 0 to about 5; z is a number from 0 to 2 in a molar ratio of about 1 mole of the substituted ureido forming compound for each mole of amine.

7. The polyether polyureide of claim 6 wherein said substituted ureido group forming compound is selected from mono substituted isocyanates and mono and disubstituted ureas.

8. The polyether polyureide of claim 7 wherein X' is a methyl radical, n is a number from 2 to 17, Z is a 1,2-propylene radical and r is about 2 or 3.

9. The polyether polyureide of claim 7 wherein A corresponds to the formula:

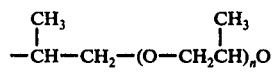

wherein n is a number from 0 to 16 and preferably a number from 1 to 10, B corresponds to the formula:

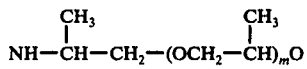

wherein m is a number from 0 to 16 and preferably a number from 1 to 10, c and d are from 1 to 2 chosen such that their sum is from 2 to 3, e is a number from 1 to 2, g is a number from 1 to 2, f is a number from 1 to 2, z is a number from 0 to 1, y is a number from 1 to 4, and X' is a C═O or C═S radical.

10. The polyether polyureide of claim 9 wherein X is the radical selected from a group consisting of

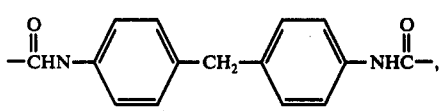

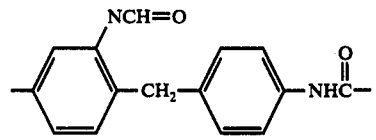

and mixtures thereof.

11. The polyether polyureide of claim 9 wherein X is a mixture of C═O and C═S radicals throughout the formula such as to yield a mixed polyether ureylenethioureylene.

12. A polyether polyureide comprising a ureido-terminated polyoxyalkylene of the formula:

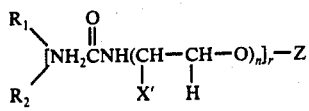

wherein $R_1$ and $R_2$ are independently hydrogen, provided only one is hydrogen; or alkyl, alkenyl, alkadienyl, alkatrienyl radicals of from 1 to 20 carbon atoms; or aryl, alkaryl or aralkyl monocyclic, polycyclic, or fused ring aromatic radicals of from 6 to 30 carbon atoms; or $R_1$ and $R_2$, taken together with the nitrogen atom to which each is attached, form a 5 or 6 membered heterocyclic ring; $X'$ is hydrogen, a methyl radical or an ethyl radical; Z is a hydrocarbon radical having 2 to 5 carbon atoms forming from 2 to 4 external ether linkages; $n$ is a number from 1 to about 20; and, $r$ is a number from 2 to 4.

13. The polyether polyureide of claim 12 wherein X; is a methyl radical; $n$ is a number from 2 to 17, Z is a 1,2-propylene radical and $r$, is about 2 or 3, $R_1$ and $R_2$ are alkyl radicals of from 1 to 4 carbon atoms; or monocyclic aryl.

14. The polyether polyureide of claim 13 wherein $r$ is 2 and the ureido terminated polyoxyalkylene has a molecular weight of about 2000.

15. The polyether polyureide of claim 13 wherein the ureido terminated polyoxyalkylene has a molecular weight of about 400.

* * * * *